US00PP36950P2

(12) United States Plant Patent
Bernuetz

(10) Patent No.: US PP36,950 P2
(45) Date of Patent: Sep. 9, 2025

(54) ***XEROCHRYSUM* PLANT NAMED 'Bonxer 1934'**

(50) Latin Name: *Xerochrysum bracteatum*
Varietal Denomination: Bonxer 1934

(71) Applicant: Andrew Bernuetz, Yellow Rock (AU)

(72) Inventor: Andrew Bernuetz, Yellow Rock (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/895,327

(22) Filed: Sep. 24, 2024

(51) Int. Cl.
*A01H 5/02* (2018.01)
*A01H 6/14* (2018.01)

(52) U.S. Cl.
USPC ..... Plt./359

(58) Field of Classification Search
USPC ..... Plt./359
See application file for complete search history.

*Primary Examiner* — Susan McCormick Ewoldt
(74) *Attorney, Agent, or Firm* — C. Anne Whealy

(57) ABSTRACT

A new and distinct cultivar of *Xerochrysum* plant named 'Bonxer 1934', characterized by its upright and mounding plant habit; vigorous growth habit; freely flowering habit; semi-double type inflorescences with light orange and bright greenish yellow-colored involucral bracts; and strong and relatively short peduncles that hold the inflorescences above and beyond the foliar plane.

2 Drawing Sheets

Figure 1:
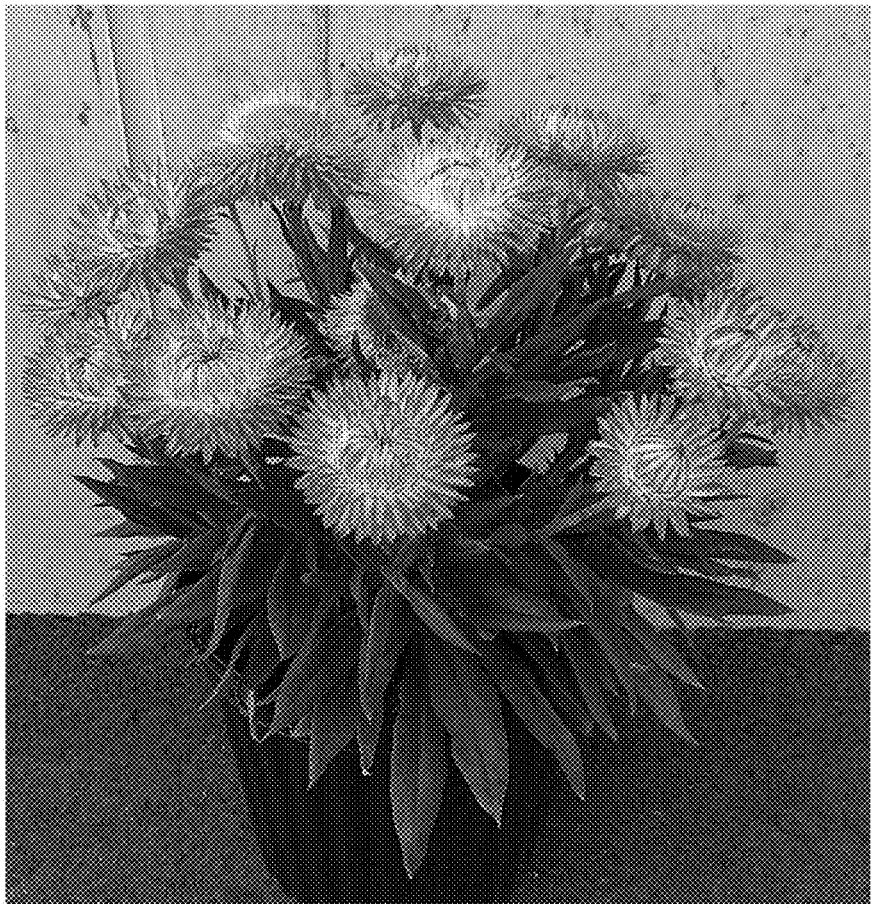

Botanical designation: *Xerochrysum bracteatum.*
Cultivar denomination: 'Bonxer 1934'.

CROSS REFERENCED TO CLOSELY-RELATED APPLICATIONS

A Japanese Plant Breeder's Rights application for the instant plant was filed by the Applicant/Assignee of the instant application, Bonza Botanicals Pty., Ltd. of Yellow Rock, New South Wales, Australia on Jul. 26, 2024, application No. 37542. Foreign priority is not claimed to this application

BACKGROUND OF THE INVENTION

The present invention relates to a new and distinct cultivar of *Xerochrysum* plant, botanically known as *Xerochrysum bracteatum*, commonly known as Strawflower, and hereinafter referred to by the name 'Bonxer 1934'.

The new *Xerochrysum* plant is a product of a planned breeding program conducted by the Inventor in Yellow Rock, New South Wales, Australia. The objective of the breeding program is to create and develop new upright *Xerochrysum* cultivars with numerous large inflorescences.

The new *Xerochrysum* plant originated from a cross-pollination by the Inventor in October, 2018 of a proprietary selection of *Xerochrysum bracteatum* identified as code No. 18-19, not patented, as the female, or seed, parent with a proprietary selection of *Xerochrysum bracteatum* identified as code No. 18-62, not patented, as the male, or pollen, parent. The new *Xerochrysum* plant was discovered and selected by the Inventor as a single flowering plant within the progeny of the stated cross-pollination in a controlled greenhouse environment in Yellow Rock, New South Wales, Australia on May 8, 2019.

Asexual reproduction of the new *Xerochrysum* plant by terminal cuttings in a controlled greenhouse environment in Yellow Rock, New South Wales, Australia since May, 2019 has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxer 1934'. These characteristics in combination distinguish 'Bonxer 1934' as a new and distinct *Xerochrysum* plant:

1. Upright and mounding plant habit.
2. Vigorous growth habit.
3. Freely flowering habit.
4. Semi-double type inflorescences with light orange and bright greenish yellow-colored involucral bracts.
5. Strong and relatively short peduncles that hold the inflorescences above and beyond the foliar plane.

In side-by-side comparisons, plants of the new *Xerochrysum* differ primarily from plants of the female parent selection in involucral bract color as inflorescences of plants of the new *Xerochrysum* have light orange and bright greenish yellow-colored involucral bracts whereas inflorescences of plants of the female parent selection have orangish yellow-colored involucral bracts.

In side-by-side comparisons, plants of the new *Xerochrysum* differ primarily from plants of the male parent selection in involucral bract color as inflorescences of plants of the new *Xerochrysum* have light orange and bright greenish yellow-colored involucral bracts whereas inflorescences of plants of the male parent selection have pale orange-colored involucral bracts.

Plants of the new *Xerochrysum* can be compared to plants of the *Bracteantha bracteata* 'Bonxero 148', disclosed in U.S. Plant Pat. No. 30,398. In side-by-side comparisons, plants of the new *Xerochrysum* differ primarily from plants of 'Bonxero 148' in the following characteristics:

1. Plants of the new *Xerochrysum* are shorter and narrower than plants of 'Bonxero 148'.
2. Leaves of plants of the new *Xerochrysum* are held horizontally whereas leaves of plants of 'Bonxero 148' are more upright.
3. Leaves of plants of the new *Xerochrysum* are longer than leaves of plants of 'Bonxero 148'.
4. Inflorescences of plants of the new *Xerochrysum* are more concave than and not as flat as inflorescences of plants of 'Bonxero 148'.
5. Inflorescences of plants of the new *Xerochrysum* are larger than inflorescences of plants of 'Bonxero 148'.
6. Inflorescences of plants of the new *Xerochrysum* have more involucral bracts than inflorescences of plants of 'Bonxero 148'.
7. Involucral bracts of plants of the new *Xerochrysum* are longer than involucral bracts of plants of 'Bonxero 148'.
8. Inflorescences of plants of the new *Xerochrysum* have light orange and bright greenish yellow-colored involucral bracts whereas inflorescences of plants of 'Bonxero 148' have bright yellow-colored involucral bracts.
9. The disc diameter of inflorescences of plants of the new *Xerochrysum* is larger than the disc diameter of inflorescences of plants of 'Bonxero 148'.
10. Peduncles of plants of the new *Xerochrysum* are shorter and thicker than peduncles of plants of 'Bonxero 148'.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph on the first sheet (FIG. 1) is a side perspective view of a typical flowering plant of 'Bonxer 1934' grown in a container.

Figure 2:
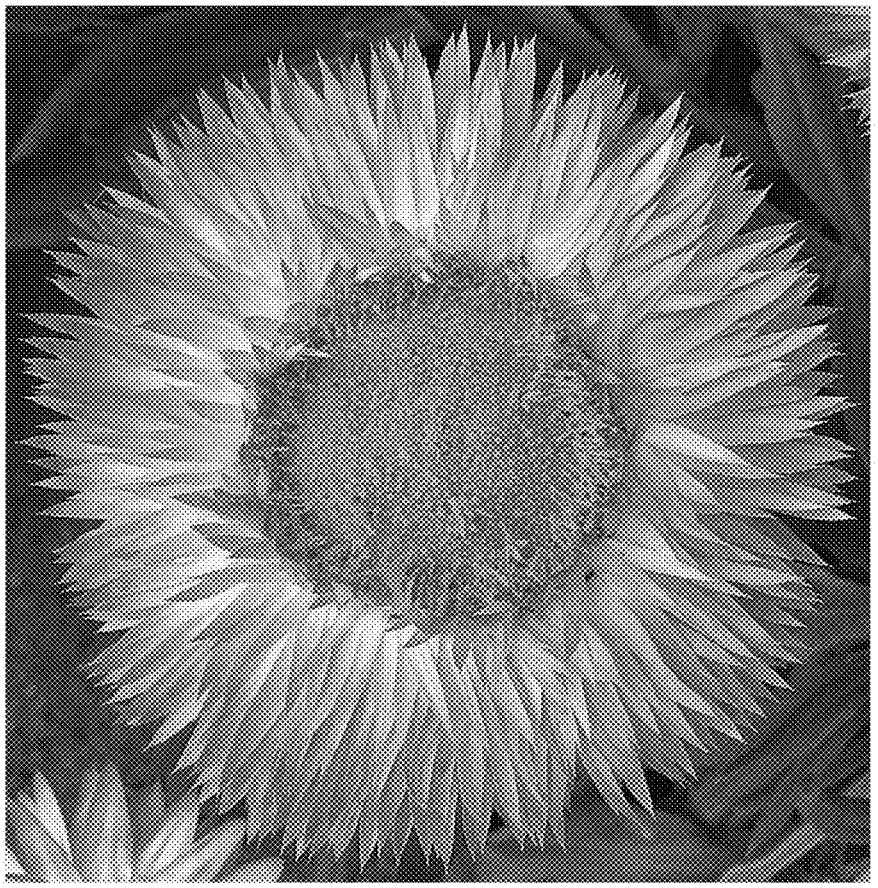

The photograph on the second sheet (FIG. 2) is a close-up view of a typical inflorescence of 'Bonxer 1934'.

DETAILED BOTANICAL DESCRIPTION

The aforementioned photographs and following observations and measurements describe plants grown during the early summer in 24-cm containers in an outdoor nursery in Higashiomi, Shiga, Japan and under conditions and practices which approximate those generally used in commercial *Xerochrysum* production. During the production of the plants, day temperatures averaged 23° C. and night averaged 13° C. Measurements and numerical values represent averages for typical flowering plants. Plants were four months old when the photographs were taken and five months old when the detailed description was taken.

In the following description, color references are made to The Royal Horticultural Society Colour Chart, 2015 Edition, except where general terms of ordinary dictionary significance are used.

Botanical classification: *Xerochrysum bracteatum* 'Bonxer 1934'.

Parentage:

*Female, or seed, parent*.—Proprietary selection of *Xerochrysum bracteatum* identified as code No. 18-19, not patented.

*Male, or pollen, parent*.—Proprietary selection of *Xerochrysum bracteatum* identified as code No. 18-62, not patented.

Propagation:

*Type*.—Terminal vegetative cuttings.

*Time to initiate roots, summer*.—About seven days at temperatures about 18° C. to 21° C.

*Time to initiate roots, winter*.—About ten days at temperatures about 18° C. to 21° C.

*Time to produce a rooted cutting, summer*.—About three weeks at temperatures about 18° C. to 21° C.

*Time to produce a rooted cutting, winter*.—About four weeks at temperatures about 18°° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Upright and mounding plant habit with inflorescences held above the foliage on strong peduncles; vigorous growth habit.

*Plant height*.—About 33.7 cm.

*Plant diameter or spread*.—About 39 cm.

*Lateral branches*.—Quantity per plant: Freely branching habit with about eight primary lateral branches with numerous secondary lateral branches developing per plant; pinching will enhance branching potential. Length: About 20 cm. Diameter: About 6.7 mm. Internode length: About 1.8 cm. Aspect: Mostly upright to slightly outwardly. Strength: Strong. Texture: Densely pubescent. Color: Close to 144A.

*Leaf description*.—Arrangement: Alternate, simple; sessile. Length: About 11.3 cm. Width: About 3 cm. Shape: Linear. Apex: Acute. Base: Attenuate. Margin: Entire; not undulate to slightly undulate. Texture, upper and lower surfaces: Rough, smooth to slightly pubescent. Venation pattern: Pinnate; reticulate. Color: Developing leaves, upper surface: Close to 137B. Developing leaves, lower surface: Close to 137C. Fully expanded leaves, upper surface: Close to 137B; venation, close to 138A. Fully expanded leaves, lower surface: Close to 137D; venation, close to 138B.

*Inflorescence description*.—Appearance: Terminal semi-double type inflorescence form with numerous ovate-shaped involucral bracts; inflorescences concave in cross-section; involucral bracts and disc florets developing acropetally on a capitulum; inflorescences positioned above the foliar plane on strong peduncles; inflorescences face mostly upright. Flowering habit: Freely flowering habit; about 16 inflorescence buds and inflorescences per plant. Fragrance: None detected. Flowering season: In the garden in Japan, plants flower continuously from the spring until the late autumn. Post-production longevity: Inflorescences maintain good substance for about seven to ten days on the plant; inflorescences persistent.

*Inflorescence buds*.—Height: About 2.1 cm. Diameter: About 1.9 cm. Shape: Ovoid with acute apex. Color: Distally, close to 184C and proximally, close to 184A.

*Inflorescence size*.—Diameter: About 7.6 cm. Depth (height): About 3.9 cm. Disc diameter: About 3.2 cm. Disc height: About 2 cm.

*Receptacles*.—Diameter: About 4.8 cm. Height: About 8.8 mm. Color: Close to 154D.

*Involucral bracts*.—Quantity per inflorescence and arrangement: About 600 arranged in numerous whorls; bracts imbricate. Length: About 2.3 cm. Width: About 7 mm. Shape: Ovate. Apex: Acuminate. Base: Truncate. Margin: Entire. Texture, upper and lower surfaces: Smooth, glabrous; papery; durable. Orientation: Initially upright becoming more outwardly with development. Color: When opening and fully opened, upper surface: Distally, close to 31C, and proximally, close to 150C; colors do not change with subsequent development. When opening and fully opened, lower surface: Distally, close to 31D, and proximally, close to 150D; colors do not change with subsequent development.

*Disc florets*.—Quantity per inflorescence and arrangement: About 632 disc florets arranged spirally in the center of the receptacle in numerous whorls. Length: About 7.3 mm. Diameter, distally: About 2.4 mm. Diameter, proximally: About 1 mm. Shape: Tubular; apex dentate, five-pointed. Texture, inner and outer surfaces: Smooth, glabrous. Color: Apex: Close to 17A. Mid-section: Close to 17C. Base: Close to 151C.

*Peduncles*.—Length: About 7.1 cm. Diameter: About 5 mm. Strength: Strong. Aspect: Mostly upright. Texture: Rough, not pubescent. Color: Close to 144A.

*Reproductive organs*.—Androecium: Quantity per disc floret: About five. Filament length: About 1.7 mm. Filament color: Close to 157D. Anther size: About 1 mm by 2.5 mm. Anther shape: Linear. Anther color: Close to 13A. Pollen: To date, none observed.

*Gynoecium*.—Quantity per disc floret: One. Pistil length: About 8 mm. Stigma shape: Bi-parted. Stigma color: Close to 14B. Style color: Close to 157D. Ovary color: Close to 155A, translucent.

*Seeds and fruits*.—To date, seed and fruit production has not been observed on plants of the new *Xerochrysum*.

Pathogen & pest resistance: To date, plants of the new *Xerochrysum* have not been observed to be resistant to pathogens and pests common to *Xerochrysum* plants.

Temperature tolerance: Plants of the new *Xerochrysum* have been observed to tolerate temperatures ranging from about 1°° C. to about 35° C.

It is claimed:

1. A new and distinct *Xerochrysum* plant named 'Bonxer 1934' as herein illustrated and described.

* * * * *